(12) United States Patent
Yin

(10) Patent No.: US 10,736,556 B2
(45) Date of Patent: Aug. 11, 2020

(54) BRAIN DISORDER EVALUATION APPARATUS

(71) Applicant: MAXELL, LTD., Kyoto (JP)

(72) Inventor: Ying Yin, Beijing (CN)

(73) Assignee: MAXELL, LTD., Kyoto (JP)

( * ) Notice: Subject to any disclaimer, the term of this patent is extended or adjusted under 35 U.S.C. 154(b) by 423 days.

(21) Appl. No.: 15/305,509

(22) PCT Filed: Apr. 20, 2015

(86) PCT No.: PCT/CN2015/076965
§ 371 (c)(1),
(2) Date: Oct. 20, 2016

(87) PCT Pub. No.: WO2015/161763
PCT Pub. Date: Oct. 29, 2015

(65) Prior Publication Data
US 2017/0112426 A1    Apr. 27, 2017

(30) Foreign Application Priority Data
Apr. 21, 2014   (CN) .......................... 2014 1 0160814

(51) Int. Cl.
*A61B 5/00* (2006.01)
*A61B 5/16* (2006.01)
(Continued)

(52) U.S. Cl.
CPC .......... *A61B 5/4064* (2013.01); *A61B 5/1124* (2013.01); *A61B 5/16* (2013.01);
(Continued)

(58) Field of Classification Search
CPC ....................................................... A61B 5/11
See application file for complete search history.

(56) References Cited

U.S. PATENT DOCUMENTS 6,422,870 B1 * 7/2002 Ohsawa .................. A61B 3/113
434/236
8,013,837 B1 * 9/2011 Schroeder ............. G06F 3/0362
345/157
(Continued)

FOREIGN PATENT DOCUMENTS

| CA | 2461272 A1 | 9/2005 |
| CN | 1521683 A | 8/2004 |

(Continued)

OTHER PUBLICATIONS

Chinese Office Action dated Oct. 19, 2018 for the Chinese Patent Application No. 201410160814.1.

*Primary Examiner* — Sean P Dougherty
(74) *Attorney, Agent, or Firm* — Volpe and Koenig, P.C.

(57) ABSTRACT

A brain disorder evaluation apparatus adjusts a prompt cycle of body movement tasks according to individual differences, and includes: a body movement prompt unit, which prompts body movement tasks to a subject; a body movement detection unit, which detects body movement data of a subject; an operation input unit, which receives the input information; an output unit; a storage unit; and a data processing unit which includes, a body movement task selection part, which selects the body movement tasks, a data obtainment part, an indicative data generation part, which generates an indication cycle by means of information input from the operation input unit and the body movement accuracy obtained by the calculations of a body movement accuracy computation part, and generates indication data according to the above-mentioned indication cycle, the body movement accuracy computation part, and a cognitive impairment degree evaluation part.

7 Claims, 4 Drawing Sheets

(51) Int. Cl.
  *A61B 5/11* (2006.01)
  *G16H 40/63* (2018.01)
  *G16H 50/70* (2018.01)
  *G16H 20/30* (2018.01)

(52) U.S. Cl.
  CPC ........... *A61B 5/4088* (2013.01); *G16H 20/30* (2018.01); *G16H 40/63* (2018.01); *G16H 50/70* (2018.01); *A61B 5/11* (2013.01); *A61B 2562/0219* (2013.01)

(56) References Cited

U.S. PATENT DOCUMENTS

| | | | | |
|---|---|---|---|---|
| 8,634,638 B2 * | 1/2014 | Han | ................... | G06K 9/00342 382/159 |
| 2002/0103429 A1 * | 8/2002 | deCharms | .............. | A61B 5/055 600/410 |
| 2002/0143240 A1 * | 10/2002 | Teicher | ................. | A61B 5/1118 600/300 |
| 2003/0233032 A1 | 12/2003 | Teicher et al. | | |
| 2009/0130640 A1 | 5/2009 | Hardy et al. | | |
| 2014/0257141 A1 * | 9/2014 | Giuffrida | ............. | A61B 5/1124 600/595 |
| 2014/0336539 A1 * | 11/2014 | Torres | ................. | A61B 5/7264 600/595 |
| 2016/0100788 A1 * | 4/2016 | Sang | ....................... | A61B 5/121 600/595 |

FOREIGN PATENT DOCUMENTS

| | | |
|---|---|---|
| CN | 1835714 A | 9/2006 |
| CN | 201200401 Y | 3/2009 |

\* cited by examiner

BRAIN DISORDER EVALUATION APPARATUS

TECHNICAL FIELD

The present invention relates to a brain disorder evaluation apparatus, and more particularly, to a brain disorder evaluation apparatus capable of adjusting a prompt cycle.

BACKGROUND

Brain disorder, such as a symptom of dementia, is a chronic or progressive syndrome caused by various brain diseases that affect memory, thinking, behavior, and ability of daily living. Alzheimer disease is the most common cause of the dementia, and is very possible to cause as high as 70% dementia cases. The World Health Organization issued and declared that there were approximately 35.60 million dementia patients in the whole world in 2012. It is anticipated that the number of the dementia patients will be double by 2030 (65.70 million), and will be triple of the present number by 2050. Every country has dementia patients, but more than half of the patients (58%) live in the low income and middle income countries. The proportion will rise to more than 70% by 2050. It will cost over 604 billion USD for treating and nursing the dementia patients in the whole world each year, comprising the charge for providing hygienic and social nursing for the dementia patients and the income losses of the dementia patients and the nursing persons thereof.

The World Health Organization also alleges that it is also a main issue to find the dementia early. Even in the high income countries, only one fifth to a half of the dementia cases are discovered in a routine examination. Moreover, the disease is usually at a terminal stage when a definite diagnosis is made.

In order to diagnose the dementia at an early stage with low cost and high efficiency, various simple evaluation apparatuses based on a tablet or a microcomputer with a touch screen are developed.

However, these apparatuses mainly tend to the evaluation to memory and an ability of judgment related to memory. Researches show that, the dementia patients have a certain difficulty on coordinated actions of arms and legs and fine actions performed under the external stimulation. Moreover, the degradation of functions of these body movements is easier to be observed at an early stage through a finger movement having higher fineness.

A brain disorder evaluation apparatus disclosed by the international application (Application No. PCT/JP2013/074582; title: Brain Disorder Evaluation Method, Brain Disorder Evaluation Apparatus, and Program Thereof) just aims at the problem, which makes a subject perform body movements according to a series of body movement tasks indicated by a system, detects the precision of the reaction speed and reaction position of the subject by a body movement detection component, compares the precision of the reaction speed and reaction position with the accuracy of a pre-prepared healthy person, and evaluates the body movement ability of the subject.

While in the prior art, a prompt interval time (prompt cycle) of the body movement task sent by the brain disorder evaluation apparatus is preset. However, because there is an individual difference between different subjects, if the prompt interval time of the body movement task aiming at each subject cannot be adjusted, it is possible to cause too short prompt interval time between the body movement tasks, and in this way, the simple bradykinesia of some old people may be possibly misjudged as dementia; or if the interval time is too long, the subject feels tired during testing, so that the measurement cannot be performed continuously.

SUMMARY

In view of the problems above, a brain disorder evaluation apparatus capable of adjusting a prompt cycle of body movement tasks according to individual differences is provided.

A brain disorder evaluation apparatus according to an embodiment of the present invention comprises: a body movement prompt unit, which prompts body movement tasks to a subject; a body movement detection unit, which detects body movement data of the subject related to the body movement made according to the body movement tasks prompted; an operation input unit, which receives the input information; an output unit, which outputs the information to the outside; a storage unit, which is able to store various pieces of data from other units; and a data processing unit, comprising: a body movement task selection part, which selects the body movement tasks input through the operation input unit or preset body movement tasks; a data obtainment part, which obtains the information input through the operation input unit, the body movement data of the body movement of the subject detected by the body movement detection unit, and the body movement accuracy obtained from a body movement accuracy computation part; an indicative data generation part, which generates an indication cycle by means of the information input from the operation input unit and obtained by the data obtainment part, and the body movement accuracy obtained by the calculations of the body movement accuracy computation part, and generates indicative data according to the body movement tasks selected by the body movement task selection part using the above-mentioned indication cycle; the body movement accuracy computation part, which computes the body movement accuracy according to the body movement data and the body movement prompt data; and a cognitive impairment degree evaluation part, which evaluates the degree of cognitive impairment according to the body movement accuracy.

According to the embodiment of the present invention, because the generation of the indication cycle is obtained according to the body movement accuracy obtained by the body movement accuracy computation part, the indication cycle can be adjusted correspondingly according to the body movement level of different groups, so as to obtain a proper indication cycle that complies with the subject group.

DETAILED DESCRIPTION

The embodiments of the present invention will be described hereinafter with reference to the drawings and specific examples.

Figure 1:
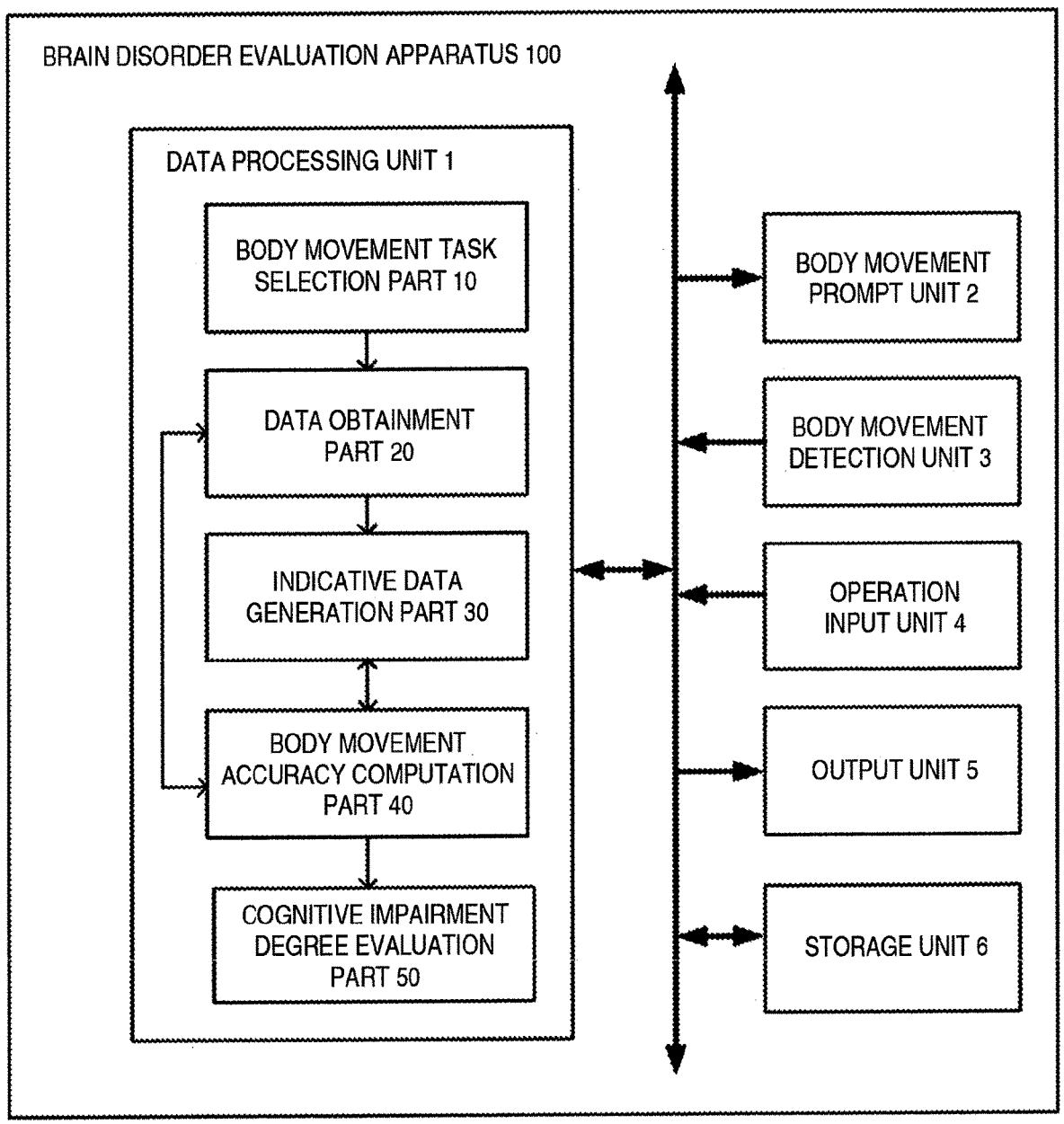
FIG. 1 is a functional block diagram illustrating an integral constitution of a brain disorder evaluation apparatus according to one embodiment of the present invention.

FIG. 1 is a functional block diagram illustrating an integral constitution of a brain disorder evaluation apparatus according to one embodiment of the present invention. As shown in FIG. 1, the brain disorder evaluation apparatus 100 according to the present invention comprises: a data processing unit 1, a body movement prompt unit 2, a body movement detection unit 3, an operation input unit 4, an output unit 5, and a storage unit 6. The data processing unit 1 usually comprises a CPU and a memory. The body movement prompt unit 2 can be composed of a display, a sound transmitter, etc. The body movement detection unit 3 is configured to detect a movement action of a subject, and can be implemented through a touch screen, an acceleration sensor, a magnetic sensor, a gyroscope apparatus, an action capture apparatus, a video shooting apparatus, and other apparatuses. The operation input unit 4 can be composed of a keyboard and a mouse, and can also be the same unit as the body movement detection unit 3. The output unit 5 can be composed of a display, a printer, or the like, and can also be implemented together with the body movement prompt unit 2 through the same apparatus. The storage unit 6 is composed of a hard disk, an SSD (Solid State Disk), or the like, and is configured to store data and programs. In addition, the data processing unit 1 can also be integrally formed with the body movement prompt unit 2, the body movement detection unit 3, the operation input unit 4, the output unit 5, and the storage unit 6.

As shown in FIG. 1, the data processing unit 1 is composed of a body movement task selection part 10, a data obtainment part 20, an indicative data generation part 30, a body movement accuracy computation part 40, and a cognitive impairment degree evaluation part 50.

The body movement task selection part 10 can select a test item implementation order prestored through the storage unit 6, and can also display an overview of the body movement tasks in the output unit 5 or the body movement prompt unit 2, and a test needed to be implemented is selected by the subject or a caregiver through the operation input unit 4.

The data obtainment part 20 obtains information input through the operation input unit 4, the body movement data of the body movement of the subject detected by the body movement detection unit 3, and the body movement accuracy obtained by the calculations of the body movement accuracy computation part 40.

The indicative data generation part 30 generates the body movement indicative data configured to prompt the subject, and prompts the indicative data generated by the indicative data generation part 30 of the data processing unit 1 to the subject through the body movement prompt unit 2. The indicative data can be an image prompt, a word prompt, and a light prompt on a liquid crystal screen, and can also be a sound prompt. The prompt on the liquid crystal screen can prompt a specific image at a specific position, and can also prompt and display a random image at a random position. The body movement prompt unit 2 can be composed of a display unit, a sound output unit, or the like.

The body movement accuracy computation part 40 computes the body movement accuracy according to the body movement data and the body movement prompt data. With regard to the calculation of the movement accuracy, a very detailed description has been made by an earlier application (PCT/JP2013/074582). According to specific requirements, for example, a weighting operation to position accuracy (i.e., the consistent degree of the movement position) and timing sequence accuracy (i.e., the speed of reaction time), etc. can be included, so as to obtain the final movement accuracy.

The cognitive impairment degree evaluation part 50 evaluates the degree of cognitive impairment according to the body movement accuracy obtained by the calculations of the body movement accuracy computation part 40.

In the past brain disorder evaluation apparatuses, the indicative data generated by the indicative data generation part is generated according to a predetermined indication cycle. However, because there is an individual difference between different subjects, if all subjects are detected according to the predetermined indication cycle, it is unable to adjust the indication interval time of the body movement task aiming at different conditions of each subject. If the interval time is too short, the simple bradykinesia of old people may be possibly misjudged as the dementia disease; or, if the interval time is too long, the subject feels tired during testing, so that the measurement cannot be made continuously.

Therefore, the indicative data generation part 30 in the embodiment can generate an indication cycle by means of the information input through the operation input unit 4 and obtained by the data obtainment part 20, and the body movement accuracy obtained by the calculations of the body movement accuracy computation part 40, so as to generate indicative data according to the body movement tasks selected by the body movement task selection part 10 based on the above-mentioned indication cycle. The information of the subject input through the operation input unit 4 here can comprise: the age, gender, health condition, and other data of the subject. The indication cycle can be adjusted through evaluating the information of the subject and the body movement accuracy of the subject obtained by the calculations of the body movement accuracy computation part 40. For example, if the body movement accuracy of the subject is higher than the average level in the age group of the subject, the indication cycle can be decreased, and if the body movement accuracy of the subject is lower than the average level in the age group of the subject, the indication cycle can be increased; or, when the body movement accuracy of the subject is continuously higher than the predetermined body movement accuracy for specified times (for example, more than five times), the indication cycle can be decreased by a specified value; and when the body movement accuracy of the subject is continuously lower than the predetermined body movement accuracy for specified times (for example, more than five times), the indication cycle can be increased by a specified value.

Figure 2:
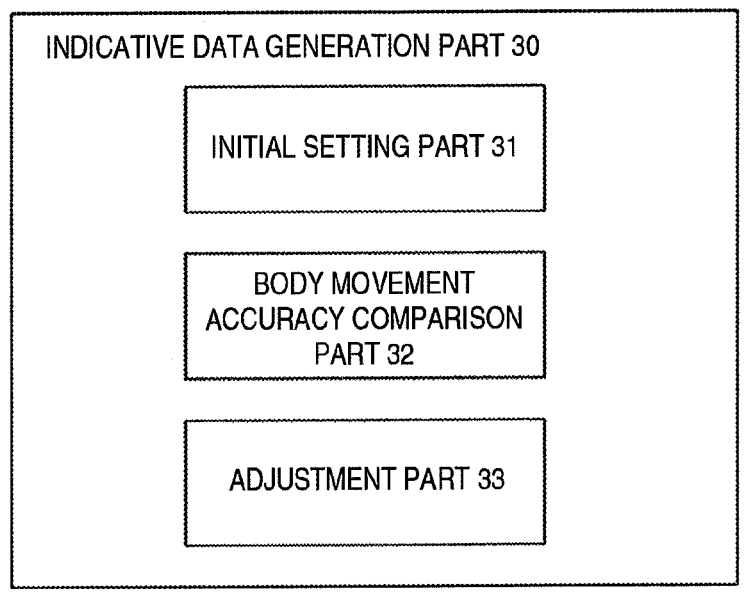
FIG. 2 is a functional block diagram illustrating an indicative data generation part in the brain disorder evaluation apparatus according to one embodiment of the present invention.
Figure 3:
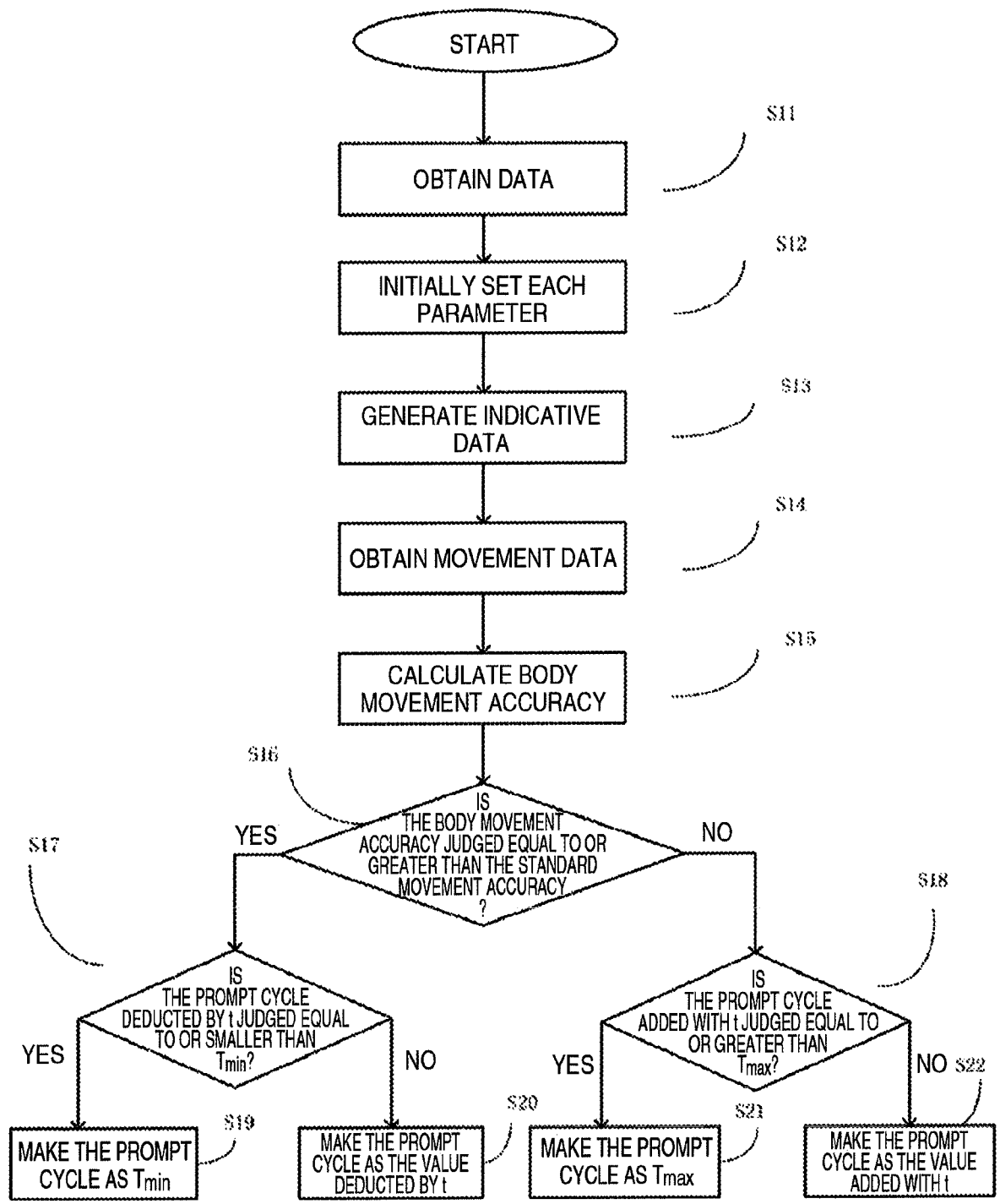
FIG. 3 is a flow diagram illustrating an action made by a prompt cycle generation part according to one embodiment of the present invention.

In addition, as another method for adjusting the indication cycle, the present invention also provides the following specific embodiment that is described in details according to FIG. 2 and FIG. 3.

<Embodiment>

FIG. 2 is a specific functional block diagram illustrating an indicative data generation part 30 according to one embodiment of the present invention, but the embodiment is used for illustration only, and is not intended to limit the scope of the present invention. As shown in FIG. 2, the indicative data generation part 30 according to one embodiment of the present invention is composed of an initial setting part 31, a body movement accuracy comparison part 32, and an adjustment part 33.

The initial setting part 31 mainly presets the following data according to various pieces of data obtained from the data obtainment part 20: an initial prompt cycle $T_0$, a maximum prompt cycle $T_{max}$, a minimum prompt cycle $T_{min}$, an adjustment degree t, and a standard movement accuracy $M_0$.

(Setting of the Initial Prompt Cycle $T_0$)

The initial prompt cycle $T_0$ is obtained through comprehensively calculating individual information, for example, the name, gender, age, of the subject input through the operation input unit 4 by the subject or the caregiver.

As an example, the following method can be listed as a manner to set the initial prompt cycle $T_0$.

To be specific, subjects at different age stages are preselected from a group of healthy people to implement the same test, and the average cycle $T_{AV}$ of the group of healthy people about 20 years old is used as a standard prompt cycle. In addition, a relationship coefficient K between the age Y of the subject and the prompt cycle is set, and the relationship coefficient can be calculated through a relationship between the actual test age and the movement ability. Then, the calculation to the initial prompt cycle conducted by the initial setting part 122 is as follows.

$$T_0 = Y*K + T_{AV}$$

(Setting of the Maximum Prompt Cycle $T_{max}$, the Minimum Prompt Cycle $T_{min}$, and the Adjustment Degree t)

The maximum prompt cycle $T_{max}$ can be set by a designer according to experimental data, for example, the maximum prompt cycle $T_{max}$ can be set as a prompt cycle that tends to be applicable to people with brain disorder. The minimum prompt cycle $T_{min}$, for example, can be set to be the same as $T_{AV}$, and can also be set as a prompt cycle that is applicable to other group of people with good movement ability.

While the adjustment degree t indicates the range of the prompt cycle adjusted in each time. The smaller the value of the adjustment degree t is, the higher the accuracy of adjustment in each time is. However, more adjustment times may be needed to reach an ideal prompt cycle, while the bigger the value of t is, the lower the accuracy of adjustment in each time is, but the fewer the adjustment times are. The setting can be performed according to actual requirements specifically.

(Setting of the Standard Movement Accuracy)

The standard movement accuracy $M_0$ can be set as an average value of a test result of normal crowds obtained through a lot of experiments, and can also be set as a proper value aiming at the old people.

The body movement accuracy comparison part 32 compares the body movement accuracy obtained by the calculations of the body movement accuracy computation part 40 with the standard movement accuracy $M_0$.

In the adjustment part 33, when the comparison result of the body movement accuracy comparison part 32 above is that the body movement accuracy obtained by the calculations of the body movement accuracy computation part 40 is equal to or greater than the standard movement accuracy $M_0$, the prompt cycle is made to be the value deducted by the adjustment degree t, and when the value deducted by the adjustment degree t is smaller than the minimum prompt cycle $T_{min}$, the prompt cycle is made to be $T_{min}$; while when the comparison result of the body movement accuracy comparison part 32 above is that the body movement accuracy obtained by the calculations of the body movement accuracy computation part 40 is smaller than the standard movement accuracy $M_0$, the prompt cycle is made to be the value added with the adjustment degree t, and when the value added with adjustment degree t is equal to or greater than the maximum prompt cycle $T_{max}$, the prompt cycle is made to be $T_{max}$.

Then, the indicative data generation part 30 generates the indicative data according to the body movement tasks selected by the body movement task selection part 10 based on the indication cycle obtained through the adjustment above.

To facilitate understanding, the movement flow of the brain disorder evaluation apparatus according to the embodiment of the present invention above is described in details hereinafter using FIG. 3.

In step S11, various pieces of data are obtained, and the step can be implemented in the data obtainment part 20 in the data processing unit 1 of the brain disorder evaluation apparatus 100. The various pieces of data comprise, for example, the individual information (comprising the age, gender, health condition, etc.) of the subject input through the operation input unit 4 by the subject or caregiver, etc. In step S12, the initial setting part 31 of the indicative data generation part 30 presets the following data: an initial prompt cycle $T_0$, a maximum prompt cycle $T_{max}$, a minimum prompt cycle $T_{min}$, an adjustment degree t, and a standard movement accuracy $M_0$. The specific setting manner is described as the context above.

Next, in step S13, the indicative data generation part 30 generates the indicative data. The generated indicative data is displayed on the body movement prompt unit 2, and the subject finishes the movement tasks according to the indicative data. If the indicative data is generated for the first time, then the indicative data is generated according to the initial prompt cycle $T_0$. In step S14, the body movement detection unit 3 obtains the movement data of the subject, and then in step S15, the body movement accuracy computation part 40 of the data processing unit 1 calculates the movement accuracy of the subject according to the movement data obtained by the body movement detection unit 3.

In step S16, the body movement accuracy comparison part 32 in the indicative data generation part 30 compares the movement accuracy of the subject obtained by the calculations in the step 15 with the standard movement accuracy $M_0$ set in the step A12, so as to judge whether the body movement accuracy obtained by the body movement detection unit 3 is equal to or greater than the standard movement accuracy. When the judgment result is yes, it indicates that the test result of the subject is preferable, and it can be considered to adjust the prompt cycle (if it is adjusted for the first time, and the prompt cycle is the initial prompt cycle $T_0$) towards a decreasing tendency. At this moment, step S17 is performed to judge whether the prompt cycle deducted by the adjustment value t is equal to or smaller than $T_{min}$. If the judgment result in the step S17 is yes, i.e., the prompt cycle deducted by the adjustment degree t is equal to or smaller than $T_{min}$, then step S19 is performed to make the prompt cycle be $T_{min}$. If the judgment result in the step S17 is no, step S20 is performed to make the prompt cycle be the value deducted by the adjustment degree t.

If the judgment result in steps 16 is no, then it indicates that the test result (accuracy) of the subject is smaller than the standard value, and at this moment, it can be considered to adjust the prompt cycle (if it is adjusted for the first time, and the prompt cycle is the initial prompt cycle $T_0$) towards an increasing tendency, and step S18 is performed to judge whether the value of the prompt cycle added with the adjustment value t is equal to or greater than $T_{max}$. If the judgment result in the step S18 is yes, i.e., the value of the prompt cycle added with the adjustment degree t is equal to or greater than $T_{max}$, then step S21 is performed to make the prompt cycle be $T_{max}$. If the judgment result in the step S18 is no, then step S22 is performed to make the prompt cycle be the value added with the adjustment degree t.

In addition, although it is not shown in the drawings, step S13 is performed after the steps S19, S20, S21, and S22. That is, in step S13, the indicative data generation part 30 generates the prompt data according to the prompt cycle adjusted.

<Variation 1>

As a variation 1 of the embodiment above, the variation 1 differs from the embodiment above in that the indicative data generation part 30 can further comprise an adjustment times counting part 34 (not shown in the drawings). The adjustment times counting part 34 presets the adjustment times N of the prompt cycle, and when the number of times that the adjustment part 32 adjusts the prompt cycle reaches the adjustment times N, the adjustment part 32 stops adjusting the prompt cycle. In this way, the adjustment times of the indicative data generation part 30 for adjusting the prompt cycle can be controlled, so as to relieve the data processing burden of the apparatus. That is, when the prompt cycle is adjusted for N times to become the relatively proper value, the prompt cycle will be used all the time for prompting. Certainly, the adjustment times N can also be amended in case that a user (the subject or the nursing person) thinks that amendment is necessary. In addition, for example, when the last prompt cycle adjustment has passed for a longer period (for example, several months), or the condition of the subject is changed, or different subjects use the same brain disorder evaluation apparatus, the adjustment times N of the adjustment part 32 can also be reset, so that a new round of prompt cycle adjustment can be performed again.

<Variation 2>

As a variation 2 of the embodiment above, the variation 2 differs from the embodiment above in that: in the embodiment, when the value of the prompt cycle deducted by the adjustment degree t is smaller than the minimum prompt cycle $T_{min}$ in the adjustment part, the prompt cycle is made equal to $T_{min}$; or when the value of the prompt cycle added with the adjustment degree t is equal to or greater than the maximum prompt cycle $T_{max}$, the prompt cycle is made equal to $T_{max}$, while in the variation 2, the adjustment degree t can also be adjusted, so that the prompt cycle is still in the range from $T_{min}$ to $T_{max}$ after the prompt cycle is added with or deducted by the adjustment degree t. To be specific, when the comparison result in the body movement accuracy comparison part is that the body movement accuracy obtained by the calculations of the body movement accuracy computation part is equal to or greater than the standard movement accuracy $M_0$, the prompt cycle is made as the value deducted by the adjustment degree t, and when the value deducted by the adjustment degree t is smaller than the minimum prompt cycle $T_{min}$, the adjustment degree t is decreased by the predetermined range and the prompt cycle is recomputed until the prompt cycle is greater than $T_{min}$; and when the comparison result in the body movement accuracy comparison part is that the body movement accuracy obtained by the calculations of the body movement accuracy computation part is smaller than the standard movement accuracy $M_0$, the prompt cycle is made as the value added with the adjustment degree t, and when the value added with adjustment degree t is equal to or greater than the maximum prompt cycle $T_{max}$, the adjustment degree t is decreased by the predetermined range and the prompt cycle is recomputed until the cycle is smaller than $T_{max}$.

The self-adjusted predetermined range of the adjustment degree can be preset according to requirements. For example, if a fine adjustment is needed, the predetermined range can be set as 25% or below, and can also be set as 50%, etc, which is not limited specifically, and can be set according to the consideration of the designer or the requirement of the user.

Figure 4:
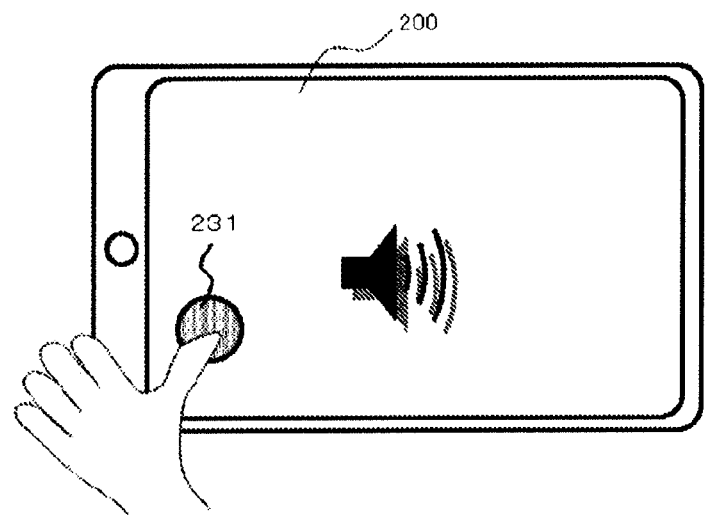
FIG. 4 is a schematic diagram illustrating a body movement task sent by a body movement prompt unit of the brain disorder evaluation apparatus according to one embodiment of the present invention.

FIG. 4 is a schematic diagram illustrating a body movement task sent by a body movement prompt unit of the brain disorder evaluation apparatus according to one embodiment of the present invention.

As shown in FIG. 4, the body movement prompt unit 2 of the brain disorder evaluation apparatus 100 is implemented as a touch screen. The indicative data generation part 30 of the data processing unit 1 generates the prompt data according to the prompt cycle and displays the prompt data on the body movement prompt unit 2. As shown in FIG. 4, a task FIG. 231 is displayed on a test screen 200 shown in the body movement prompt unit 2, and an indication sound is transmitted through a loudspeaker and other equipment at the same time, to prompt the occasion to press the rounded task FIG. 231 to a tester. The tester cooperates with the prompt cycle to press the task FIG. 231 repeatedly. In addition, the body movement accuracy computation part 40 calculates the body movement accuracy according to the position (such as X and Y in a coordinate system) pressed by the subject and the occasion of pressing by the subject.

The contents above describe several embodiments of the present invention, but these embodiments are only for illustration and are not intended to limit the scope of the present invention. Various omission, replacement, alteration, and combination can be made to these embodiments through various other forms, without departing from the scope and spirit of the present invention. These embodiments and deformations thereof shall fall within the scope and spirit of the present invention, and shall also fall within the scope of the present invention and the equivalency thereof recorded in the claims.

The invention claimed is:

1. An apparatus for testing brain disorders, the apparatus comprising:
   a display;
   a sensor that detects body movement data of a subject;
   a memory; and
   a processor that is communicatively coupled to the display, the sensor, and the memory, wherein the processor is configured to:
   obtain information about the subject, wherein the information about the subject includes at least one of an age, gender and health condition,
   retrieve initial parameters from the memory based on the information about the subject, wherein the initial parameters include a standard movement accuracy and an initial prompt interval,
   collect, using the sensor and the display, first body movement data for the subject, wherein the first body movement data is collected based on the initial prompt interval;
   compute a first body movement accuracy based on the first body movement data,
   set a second interval based on a comparison of the first body movement accuracy to the standard movement accuracy,
   collect, using the sensor and the display, second body movement data for the subject, wherein the second body movement data is collected based on the second interval, compute a second body movement accuracy based on the second body movement data, and calculate data indicative of a degree of cognitive impairment of the subject based on the second body movement data and the second body movement data wherein the processor is configured to set the second interval to be:

shorter than the initial interval when the first body movement accuracy is greater than the standard movement accuracy, and longer than the initial interval when the first body movement accuracy is not greater than the standard movement accuracy.

2. The apparatus according to claim 1, wherein the initial parameters further include a degree of adjustment, and the processor is further configured to:

form the second interval that is shorter than the initial interval by subtracting the degree of adjustment from the initial interval, and form the second interval that is longer than the initial interval by adding the degree of adjustment to the initial interval.

3. The apparatus according to claim 1, wherein the body movement accuracy is calculated according to a position accuracy representing a consistent degree of positions computed from the body movement data.

4. An apparatus for testing brain disorders, the apparatus comprising:

a display;

a sensor that detects body movement data of a subject;

a memory that stores initial parameters, wherein the initial parameters include:

an initial prompt cycle $T_o$, a maximum prompt cycle $T_{max}$, a minimum prompt cycle $T_{min}$, an adjustment degree t, and a standard movement accuracy $M_o$;

a processor that is communicatively coupled to the display, the sensor, and the memory, wherein the processor is configured to:

obtain information about the subject, wherein the information about the subject includes at least one of an age, gender and health condition, retrieve particular initial parameters from the memory based on the information about the subject, perform a data collection cycle that gathers body movement data for the subject, wherein the data collection cycle includes:

collecting, using the sensor and the display, respective body movement data for the subject, wherein the respective body movement data is collected based on the initial prompt cycle $T_o$ in a first instance of the data collection cycle an a calculated interval in subsequent instances of the data collection cycle, computing a respective body movement accuracy based on the respective body movement data collected, and calculating the calculated interval based on a comparison of the respective body movement accuracy to the standard movement accuracy $M_o$, calculate data indicative of a degree of cognitive impairment of the subject based on the body movement data gathered by the data collection cycle wherein on a condition that that the respective body accuracy is equal to or greater than $M_o$, the processor is configured to calculate the calculated interval by, by subtracting the adjustment degree t from the calculated interval to form a new interval, setting the new interval equal to $T_{min}$, when the new interval is smaller than the minimum prompt cycle $T_{min}$; and setting the calculated interval equal to the new interval;

wherein on a condition that the respective body accuracy is smaller than the standard movement accuracy $M_o$, the processor is configured to calculate the calculated interval by:

adding the adjustment degree t to the calculated interval to form the new interval, setting the new interval to $T_{max}$ when the new interval is equal to or greater than the maximum prompt cycle $T_{max}$, and setting the calculated interval equal to the new interval.

5. The apparatus according to claim 4, wherein the data collection cycle further includes calculating a number of times that the data collection cycle has been performed, and not calculating the calculated interval based on the comparison of the respective body movement accuracy after the data collection cycle has been performed a predetermined number of times.

6. The brain disorder evaluation apparatus according to claim 4, wherein the data collection cycle further includes:

determining a new adjustment degree when the new interval is smaller than the minimum prompt cycle $T_{min}$, wherein the new adjustment degree is determined by decreasing the adjustment degree t by a predetermined range; and determine the new adjustment degree when the new interval is equal to or greater than the maximum prompt cycle $T_{max}$, wherein the new adjustment degree is determined by decreasing the adjustment degree t by the predetermined range.

7. The apparatus according to claim 6, wherein, the predetermined range of the adjustment degree is 25% to 50%.

* * * * *